United States Patent [19]

Crivello et al.

[11] 4,238,619

[45] Dec. 9, 1980

[54] METHOD FOR MAKING ARYL ONIUM SALTS OF GROUP VIA ELEMENTS

[75] Inventors: James V. Crivello, Clifton Park; Julia H. W. Lam, Schenectady, both of N.Y.

[73] Assignee: General Electric Company, Schenectady, N.Y.

[21] Appl. No.: 46,116

[22] Filed: Jun. 6, 1979

Related U.S. Application Data

[63] Continuation of Ser. No. 954,196, Oct. 24, 1978, which is a continuation of Ser. No. 833,279, Sep. 14, 1977, abandoned.

[51] Int. Cl.$^2$ ................. C07D 335/12; C07D 497/00
[52] U.S. Cl. ........................................ 549/3; 260/333; 260/429 R; 260/429.1; 260/429.2; 260/429.3; 260/429.5; 260/429.7; 260/438.5 R; 260/439 R; 260/440; 260/446; 260/447 R; 260/448 R; 568/6; 568/14
[58] Field of Search ............... 549/3; 260/333, 429 R, 260/429.1, 429.3, 429.5, 429.7, 438.5 R, 439 R, 440, 446, 447 R, 448 R, 606 B, 606 P; 544/1, 38

[56] References Cited

U.S. PATENT DOCUMENTS

| | | | |
|---|---|---|---|
| 4,047,923 | 9/1977 | Naumann et al. | 71/76 |
| 4,058,400 | 11/1977 | Crivello | 96/86 P |

OTHER PUBLICATIONS

Olah et al., J. Am. Chem. Soc., vol. 92, pp. 2562 to 2564 (1970).
Nesmeyanov et al., Tetrahedron, vol. 1, pp. 145–157 (1957).
Sneed et al., Comprehensive Inorganic Chemistry, vol. 2, p. 106, D Van Nostrand Co., NY (1954).
Kirk–Othmer, Encyclopedia of Chemical Technology, 2nd ed., vol. 6, p. 267, John Wiley and Sons, Inc. (1965).

*Primary Examiner*—John D. Randolph
*Attorney, Agent, or Firm*—William A. Teoli; James C. Davis, Jr.

[57] ABSTRACT

A method is provided for making certain aryl onium salts of Group VIa elements useful as photoinitiators for polymerizing various organic materials. Reaction is effected between a compound of a Group VIa element, for example, an aryl or alkyl sulfide or a thiophenol or mercaptan and an aromatic iodonium salt in the presence of a copper compound catalyst or a copper compound-tertiary amine cocatalyst.

8 Claims, No Drawings

METHOD FOR MAKING ARYL ONIUM SALTS OF GROUP VIA ELEMENTS

This is a continuation of application Ser. No. 954,196, filed Oct. 24, 1978, which is a continuation of Ser. No. 833,279, filed Sept. 14, 1977, now abandoned.

The present invention relates to a method for making Group VIa aromatic onium salts. More particularly, the present invention relates to a reaction between an aromatic iodonium salt and a compound of a Group VIa element in the presence of a copper compound catalyst or a copper compound-tertiary amine cocatalyst.

Prior to the present invention, various methods were available for making aryl onium salts of the formula, $$[(R)_a(R^1)_b(R^2)_cX]^{d+}[MQ_e]^{-(e-f)}$$

where R is a monovalent aromatic organic radical, $R^1$ is monovalent organic aliphatic radical, selected from alkyl, cycloalkyl and derivatives thereof, $R^2$ is a polyvalent organic radical forming a heterocyclic or fused ring structure, selected from aliphatic radicals and aromatic radicals, X is a Group VIa element selected from sulfur and selenium, M is a metal or metalloid, Q is a halogen radical, "a" is a whole number equal to 0 to 3 inclusive,
"b" is a whole number equal to 0 to 2 inclusive,
"c" is a whole number equal to 0 or 1 and the sum of "a" + "b" + "c" is a value equal to 3 or the valence of X,
"d" is equal to e-f,
"e" is greater than "f" and is an integer having a value up to 8,
"f" is equal to the valence of M and is an integer equal to from 2 to 7 inclusive. One procedure is shown by Nesmeyanof et al, Tetrahedron 1, 145 (1957), involving the direct condensation of diaryl iodonium salts with diaryl sulfides to produce triarylsulfonium salts. This procedure resulted in a 60% yield of triphenylsulfonium tetrafluoroborate at temperatures in the range of 220°–230° C. Following the same procedure, Knapczyk et al, J. Org. Chem., 35, 2539 (1970) found that 35 hours were required at temperatures of 185° C. In addition, the procedure appeared limited to the production of triarylsulfonium salts as attempts to prepare substituted derivatives resulted in very poor yields.

The present invention is based on the discovery that higher yields of aromatic sulfonium salts including substituted derivatives thereof can be obtained at lower reaction temperatures and enhanced reaction rates by employing a copper salt catalyst in combination with the aryl iodonium salt and aryl sulfide or alkyl sulfide. A typical reaction, for example, would be the reaction between diphenyliodonium hexafluoroarsenate and diphenylsulfide in the presence of a copper benzoate catalyst to produce a 97% yield of triphenylsulfonium hexafluoroarsenate at 120° C. for three hours.

In accordance with the present invention, there is provided a method for making aryl onium salts of formula (1) which comprises (A) effecting reaction between a diaryl iodonium salt of the formula $$[(R)_g(R^2)_h I]_{d'}{}^+[M'Q'_e]^{-(e'-f')},$$

and from 1 to 5 moles, per mole of such diaryl iodonium salt of a Group VIa compound of the formula, $$(R)_j(R^1)_k(R^2)_mX',$$

in the presence of an effective amount of a copper salt, where R, $R^1$ and $R^2$ are as previously defined, M' is a metal or metalloid, Q' is a halogen radical, X' is a Group VIa element, "g" is a whole number equal to 0 to 2 inclusive,
"h" is a whole number equal to 0 or 1, and the sum of g+h is equal to 2 or the valence of I,
"j" is a whole number equal to 0 to 2 inclusive,
"k" is a whole number equal to 0 to 2,
"m" is a whole number equal to 0 or 1 and the sum of j+k+m is a value equal to 2 or the valence of X',
d' is equal to e'−f',
e' is greater than f' and is an integer having a value of up to 8,
f' is equal to the valence of M and is an integer equal to from 2 to 7 inclusive.

In addition to the above described method for making aromatic onium salts of Group VIa elements using Group VIa compounds of formula 3, there also can be employed in the practice of the method of the present invention, a sulfur compound of the formula, $$R^3SH, \qquad (4)$$

where $R^3$ is selected from $C_{(5-12)}$ alkyl radicals and $C_{(6-13)}$ aromatic radicals. It has been found that in using compounds of formula 4, such as thiophenols or alkyl mercaptans that a cocatalyst of the copper compound and a trialkyl amine can be employed.

Radicals included by R are, for example, $C_{(6-13)}$ aromatic hydrocarbon radicals such as phenyl, tolyl, napthyl, anthryl, and such radicals substituted with up to 1 to 4 monovalent radicals such as $C_{(1-18)}$ alkoxy, $C_{(1-8)}$ alkyl, nitro, chloro, hydroxy, etc.; arylacyl radicals such as benzyl, phenylacyl, etc.; aromatic heterocyclic radicals such as pyridyl, furfuryl, etc. $R^1$ radicals include $C_{(1-8)}$ alkyl, such as methyl, ethyl, etc., substituted alkyl such as $-C_2H_4OCH_3$, $-CH_2COOC_2H_5$, $-CH_2COCH_3$, etc. $R^2$ radicals include such structures as:

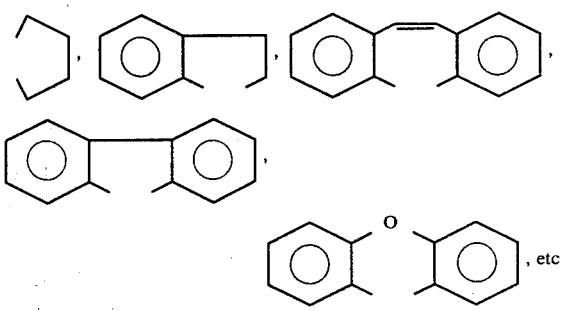

There are included by the copper salt catalysts, copper halides, such as CuCl, CuBr, $CuCl_2$; $CuSO_4$, $Cu(O_2C-CH_3)_2$, $Cu(O_2C-CH_3)_2$, $Cu(O_2C-C_6H_5)$, $Cu(O_2C-C_{17}H_{35})_2$, Copper acetylacetonate, $CuNO_3$, $Cu(O_2CH)_2$, $CuCO_3$, etc.

There are included by the tertiary amine catalysts which can be used with the above copper salts as cocatalysts trialkyl amines, such as $(C_2H_5)_3N$, $(C_4H_9)_3N$, $(C_3H_7)_3N$, $(CH_3)_3N$, $C_6H_5N(CH_3)_2$, $C_6H_4\text{—}CH_2N(CH_3)_2$,

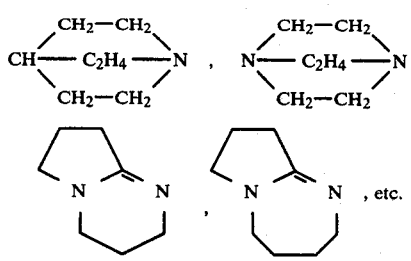

Complex anions included by $MQ_e^{-(e-f)}$ and $M'Q'_{e'}^{-(e'-f)}$ of formulas (1) and (2) are, for example, $BF_4^-$, $PF_6^-$, $AsF_6^-$, $SbF_6^-$, $FeCl_4^-$, $SnCl_6^-$, $SbCl_6^-$, $BiCl_5^-$, $AlF_6^{-3}$, $GaCl_4^-$, $InF_4^-$, $TiF_6^-$, $ZrF_6^-$, etc., where M and M' are transition metals such as Sb, Fe, Sn, Bi, Al, Ga, In, Ti, Zr, Sc, V, Cr, Mn, Cs, rare earth elements such as the lanthanides, for example, Ce, Pr, Nd, etc., actinides, such as Th, Pa, U, Np, etc., and metalloids such as B, P, As, etc., and Q and Q' are halogen atoms such as chlorine, fluorine, bromine, etc.

Included by the compounds shown by formula (3) are, for example, aromatic sulfides such as diphenyl sulfide, 4,4'-dimethyldiphenyl sulfide, 4,4'-dichlorodiphenyl sulfide, 3,3'-dinitrodiphenyl sulfide, 3-nitrophenyl phenyl sulfide, 4,4'-dihydroxydiphenyl sulfide, thioxanthene, dibenzothiophene, benzo-β-thiophene, phenoxanthene, etc. Aliphatic sulfides, such as tetrahydrothiophene, dimethylsulfide, diethylsulfide, pentamethylene sulfide, 1,4-thioxane, dibutyl sulfide, thioanisole.

Included by the compounds of formula (4) are, for example, thiophenyl, 4-fluorothiophenyl, thiocresol, 4-chlorothiophenyl, 4-hydroxythiophenol, 1,4-dimercaptobenzene, 4-nitrothiophenol, cyclohexanethiol, 1-hexylmercaptan, etc.

In formula (4), for example aromatic radicals included by $R^3$ are, for example, phenyl, tolyl, naphthyl, xylyl, anthryl, etc.; alkyl radicals included by $R^3$ are, for example, pentyl, hexyl, heptyl, octyl, nonyl, decyl, etc.

The diaryliodonium salts of formula (2) and methods for making them are shown in Crivello patent 3,981,897. Additional methods for making such iodonium salts are shown by R. B. Sandin, Chem. Rev., 32, 249 (1943); I. Masson, Nature, 139, 150 (1937); I. Masson and E. Race, J. Chem. Soc., 1718 (1937), I. Mason and W. E. Handy, J. Chem. Soc., 1966 (1937), I. Masson and C. Arugurment, J. Chem. Soc., 1703 (1938), F. M. Beringer, R. A. Falk, M. Karmal, J. Lillien, G. Masullo, M. Mausner and E. Sommer, J. Am. Chem. Soc., 81, 342 (1958).

Some of the aryl onium salts of formula (1) are shown in copending application of James V. Crivello, RD-10218, filed concurrently herewith and assigned to the same assignee as the present invention. There are included by such onium salts compounds such as

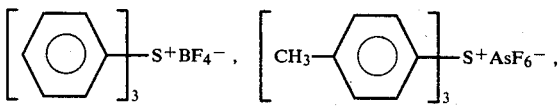

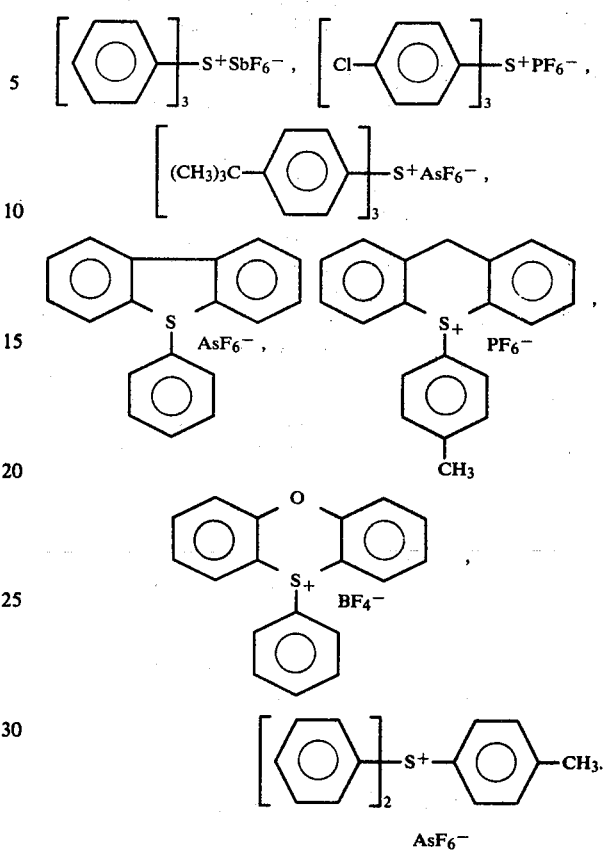

In the practice of the invention the aryl onium salts of formula (1) can be made by effecting reaction between the aryl iodonium salt of formula (2) and the Group VIa compound of formula (3) in the presence of an effective amount of the copper salt catalyst or cocatalyst thereof.

Reaction between the Group VIa compound of formula (3) and the aryl iodonium salt of formula (2) can be effected in the melt while temperatures in the range of from 50° C. to 250° C. with stirring will provide for effective results. A nonpolar inert organic solvent also can be employed if desired, such as chlorobenzene, benzonitrile, dimethylformamide, o-dichlorobenzene, etc. The copper salt catalyst can be employed at from 0.01% to 10% by weight based on the weight of the total reaction mixture and preferably from 0.1% to 3%.

In certain cases, the Group VIa onium salts of formula (1) can be made by use of thio compounds of formula (4) in combination with the diaryl iodonium salt of formula (2) in the presence of both a copper salt catalyst as described above and in forther combination with a trialkyl amine. The copper salt trialkyl amine cocatalyst can be used at the above copper salt weight basis and there can be employed from 0.5 moles to 5 moles of trialkyl amine per mole of the thio compound. The conditions employed for the synthesis of the Group VIa onium salts utilizing the thio compound approach also can be conducted in the absence of or in the presence of the above-described inert nonpolar organic solvent which can be utilized at from 50% to 500% by weight of the total reaction mixture.

Recovery of the aryl onium salt of formula (1) can be achieved by standard techniques by pouring the reaction mixture while it is hot into a suitable container and allowing it to crystallize. Standard procedures such as extraction with a suitable extracting solvent can provide for the recovery of substantially pure aryl onium salt following standard methods.

The aryl onium salts of Group VIa elements made in accordance with the method of the present invention can be used to effect the photoinitated cationic polymerization of various organic materials such as described in the copending applications Ser. Nos. 638,981, now U.S. Pat. No. 4,058,540, and 638,982, now U.S. Pat. No. 4,058,401, filed Dec. 9, 1975 as well as in the copending application Ser. No. 833,146, filed Sept. 14, 1977, now U.S. Pat. No. 4,161,478 issued July 12, 1972, to effect free-radical cures of various organic materials as shown in copending application of James V. Crivello and James E. Moore, Ser. No. 822,220, filed Aug. 5, 1977, now abandoned, where all of these applications are assigned to the same assignee as the present invention.

In order that those skilled in the art will be better able to practice the present invention, the following examples are given by way of illustration and not by way of limitation. All parts are by weight.

EXAMPLE 1

A mixture of 11.75 parts of diphenyl iodonium hexafluoroarsenate, 4.065 parts of diphenyl sulfide and 0.2 part of copper benzoate was heated with stirring at a temperature of 120°–125° C. for 3 hours. The mixture was then poured while it was hot into a container whereupon the product crystallized. The product was extracted three times with diethylether and then air dried. There was obtained a 97% yield of triphenylsulfonium hexafluoroarsenate. The triphenylsulfonium hexafluoroarsenate product had a melting point of 195°–197° C. after it was further recrystallized from 95% ethanol.

A mixture of 0.02 mole solution of the triphenylsulfonium hexafluoroarsenate in styrene oxide was irradiated at 25° C. in a glass vial sealed under nitrogen using a 450 watt Hanovia lamp. It was found that the styrene oxide polymerized after 5 minutes. The same procedure was repeated except that there was used tetrahydrofuran.

EXAMPLE 2

The procedure of Example 1 was repeated, except that there was ued 11.75 parts of diphenyliodonium hexafluoroarsenate, 2.55 parts of pentamethylene sulfide and 0.2 part of copper benzoate. A 60% yield of product, namely, phenyl pentamethylenesulfonium hexafluoroarsenate was obtained after the product was recrystallized from ethanol.

EXAMPLE 3

A mixture of 2.75 parts of thiophenol, 11.75 parts of diphenyliodonium hexafluoroarsenate and 0.2 part copper benzoate and 4.63 parts of tri-n-butyl amine was heated at 120°–125° C. under nitrogen for three hours. There was obtained an 86% yield of product upon cooling which was washed and dried. The product was triphenylsulfonium hexafluoroarsenate.

EXAMPLE 4

A mixture was heated with stirring under nitrogen of 4.6 parts of dibenzothiophene, 9.25 parts of diphenyliodonium fluoroborate and 0.2 part of copper benzoate at 210° C. for 30 minutes. The reaction mixture was allowed to cool to room temperature resulting in a crystalline product. The product was washed several times with anhydrous diethylether and then collected by filtration. Recrystallization from methylene chloride-ethyl ether gave a 55% yield of pure S-phenyldibenzothiophenium fluoroborate having a melting point of 237°–242° C. and the formula,

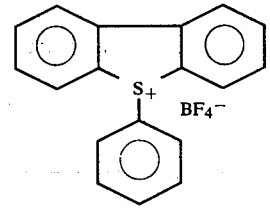

| Analysis | % C | % H | % S |
| --- | --- | --- | --- |
| calc: | 62.10 | 3.77 | 9.21 |
| found: | 61.86 | 3.60 | 9.02 |

The above sulfonium salt is used to photopolymerize styrene oxide as a 2% solution.

EXAMPLE 5

A mixture of 9.25 parts of diphenyliodonium fluoroborate, 4.95 parts of thioxanthene and 0.2 part of copper benzoate was heated with stirring for 3 hours under a nitrogen atmosphere. A crystalline product was treated on cooling with ethyl ether and then recrystallized from methylene chloride-ethyl ether. A 60% yield of a pale yellow product was obtained having a melting point of 168°–169° C. It was identified by its elemental analysis and nuclear magnetic resonance spectrum to be S-phenylthioxanthylium fluoroborate having the formula,

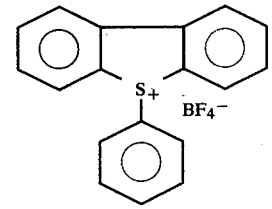

The above sulfonium salt when dissolved as a 3% solution in 4-vinylcyclohexane dioxide and irradiated using a G.E. H3T7 lamp at a distance of 6 inches cured in 30 seconds to a hard, tack-free film.

EXAMPLE 6

A mixture of 12.75 parts of 4,4'-diisopropylphenyliodonium hexafluoroarsenate, 5 parts of phenoxanthene and 0.2 part of copper benzoate was heated with stirring at 120°–125° C. for 3 hours. After cooling, the product was extracted with diethylether. The remaining oil was dissolved in methylene chloride and passed through a six inch column of alumina. Trituration with ether followed by cooling in an ice bath gave a white product amounting to 41% yield of 4-isopropylphenylphenoxanthylium hexafluoroarsenate (m.p. 126°–127° C.) having the formula,

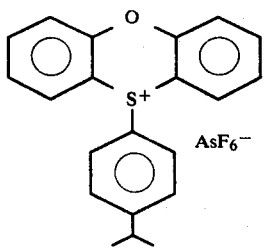

| Analysis | % C | % H | % S |
|---|---|---|---|
| calc: | 49.60 | 3.74 | 6.30 |
| found: | 49.57 | 3.82 | 6.25 |

When dissolved as a 3% solution in 3,4-epoxycyclohexylmethyl-3',4'-epoxycyclohexane carboxylate and irradiated with a G.E. H3T7 lamp at a distance of 10 inches, the above triarylsulfonium salt gave a hard tack-free film in 30 seconds.

In addition to the diaryliodonium salt of formula (2), the aryl onium salts of formula (1) also can be made by the method of the present invention using diaryliodonium salts of the formula, $$[(R)_g(R^2)_hI] [Y]^-$$

where R, $R^2$, g and h are as previously defined and Y is a non-nucleophilic counter ion selected from $M'Q'_{d'}$ and Z, where $M'Q'_{e'}$ is as previously defined and Z is is selected from $ClO_4$, $FPO_3$, $CF_3SO_3$ and $CH_3-C_6H_5SO_3$.

Although the above examples are directed to only a few of the very many variables involved in the practice of the present invention, it should be understood that the present invention can be carried out in a much broader manner as shown by the teaching in the specification preceding these examples.

What we claim as new and desire to secure by Letters Patent of the United States is:

1. In a method for making aryl organic onium salts of a Group VIa element selected from the class consisting of sulfur and selenium which comprises reaction at temperatures exceeding 185° C., an aryl organic iodonium salt and an organic compound of the Group VIa element selected from aryl organic compounds, aliphatic organic compounds and cycloaliphatic organic compounds whereby extended reaction times are required and less than 60% yields of the aryl organic onium salt of the Group VIa element result, the improvement which comprises, effecting the reaction of the organic compound of the Group VIa element and the aryl organic iodonium salt in the presence of an effective amount of copper catalyst resulting in improved yields of the aryl organic onium salt of the Group VIa element at a reduced temperature and reaction time.

2. A method in accordance with claim 1, where the organic compound of the Group VIa element is an organic sulfur compound and the copper catalyst is in the form of a cocatalyst of a copper compound and a trialkyl amine.

3. A method in accordance with claim 1, which is carried out in the melt.

4. A method for making triphenylsulfonium hexafluoroarsenate which comprises
   (A) effecting reaction between diphenyliodonium hexafluoroarsenate and diphenylsulfide in the presence of copper benzoate under melt conditions and
   (B) extracting the resulting product with an organic solvent.

5. A method in accordance with claim 2, where the organic sulfur compound is a thiophenol.

6. A method in accordance with claim 2, where the organic sulfur compound is an alkyl mercaptan.

7. A method for making triphenylsulfonium hexafluoroarsenate which comprises
   (A) effecting reaction between diphenyliodonium hexafluoroarsenate and thiophenol in the presence of an effective amount of a copper benzoate tri-n-butyl amine cocatalyst under melt conditions and
   (B) extracting the resulting crystalline product with an organic solvent.

8. A method for making 4-isopropylphenylphenoxanthylium hexafluoroarsenate, which comprises reaction 4,4'-diisopropyldiphenyliodonium hexafluoroarsenate and phenoxanthene in the presence of copper benzoate.

* * * * *